(12) United States Patent
Kay et al.

(10) Patent No.: US 9,259,251 B2
(45) Date of Patent: *Feb. 16, 2016

(54) ORTHOPEDIC PLATE FOR USE IN SMALL BONE REPAIR

(71) Applicant: ORTHOHELIX SURGICAL DESIGNS, INC., Medina, OH (US)

(72) Inventors: David B. Kay, Akron, OH (US); Lee A. Strnad, Broadview Hts., OH (US); Dustin Ducharme, Stow, OH (US); G. Martin Wynkoop, Gainesville, FL (US)

(73) Assignee: ORTHOHELIX SURGICAL DESIGNS, INC., Medina, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,207

(22) Filed: Mar. 31, 2014

(65) Prior Publication Data

US 2014/0296924 A1 Oct. 2, 2014

Related U.S. Application Data

(60) Continuation of application No. 13/348,888, filed on Jan. 12, 2012, which is a division of application No. 12/380,177, filed on Feb. 24, 2009, now Pat. No. 8,118,846, which is a continuation-in-part of (Continued)

(51) Int. Cl.
*A61B 17/80* (2006.01)
*A61B 17/88* (2006.01)
*A61B 17/56* (2006.01)

(52) U.S. Cl.
CPC ......... *A61B 17/8061* (2013.01); *A61B 17/8057* (2013.01); *A61B 17/8085* (2013.01); *A61B 17/56* (2013.01); *A61B 17/8004* (2013.01); *A61B 17/885* (2013.01)

(58) Field of Classification Search
CPC ........... A61B 17/8061; A61B 17/8004; A61B 17/8085
See application file for complete search history.

(56) References Cited

U.S. PATENT DOCUMENTS 2,526,959 A 10/1950 Lorenzo
3,716,050 A 2/1973 Johnston
(Continued)

FOREIGN PATENT DOCUMENTS

CH 611147 A5 5/1979
DE 20309361 U1 5/1979
(Continued)

OTHER PUBLICATIONS

Locking Clavicle Plate System by ACUMED(R), Brochure, 7 pages, Jul. 2005.
(Continued)

*Primary Examiner* — Ellen C Hammond
(74) *Attorney, Agent, or Firm* — Hudak, Shunk & Farine Co. LPA (57) ABSTRACT

The present invention relates to a series of orthopedic plates for use in repair of a bone. The plate has a Y-shaped profile or an X-shaped profile which includes an elongate central trunk with a complex contour and either one or two terminal pairs of arms that have a first arm and a second arm that form differing angles and lengths relative to the trunk portion of the plate. The arms include locking screw holes where the screws converge toward each other to provide for multiplanar fixation but which do not impinge.

24 Claims, 10 Drawing Sheets

Related U.S. Application Data application No. 11/340,028, filed on Jan. 26, 2006, now Pat. No. 7,771,457.

(60) Provisional application No. 60/648,364, filed on Jan. 28, 2005.

(56) References Cited

U.S. PATENT DOCUMENTS

| | | | |
|---|---|---|---|
| 4,867,144 | A | 9/1989 | Karas et al. |
| 4,903,691 | A * | 2/1990 | Heinl ............................ 606/70 |
| 5,304,180 | A | 4/1994 | Slocum |
| 5,324,290 | A | 6/1994 | Zdeblick et al. |
| 5,569,250 | A | 10/1996 | Sarver et al. |
| 5,681,311 | A | 10/1997 | Foley et al. |
| 5,690,631 | A | 11/1997 | Duncan et al. |
| 5,718,705 | A | 2/1998 | Sammarco |
| 5,749,872 | A | 5/1998 | Kyle et al. |
| 5,766,175 | A | 6/1998 | Martinotti |
| 5,853,413 | A | 12/1998 | Carter et al. |
| 6,030,389 | A | 2/2000 | Wagner et al. |
| 6,096,040 | A | 8/2000 | Esser |
| 6,123,709 | A | 9/2000 | Jones et al. |
| D449,692 | S | 10/2001 | Michelson |
| 6,358,250 | B1 | 3/2002 | Orbay |
| 6,454,769 | B2 | 9/2002 | Wagner et al. |
| 6,527,776 | B1 | 3/2003 | Michelson |
| 6,565,570 | B2 | 5/2003 | Sterett et al. |
| 6,575,975 | B2 | 6/2003 | Brace et al. |
| 6,585,769 | B1 | 7/2003 | Muhanna et al. |
| 6,623,486 | B1 | 9/2003 | Weaver et al. |
| D520,637 | S | 5/2006 | Kay et al. |
| 7,052,499 | B2 | 5/2006 | Steger et al. |
| 7,108,697 | B2 | 9/2006 | Mingozzi et al. |
| 7,128,744 | B2 | 10/2006 | Weaver et al. |
| 7,166,111 | B2 | 1/2007 | Kolb et al. |
| 7,341,589 | B2 | 3/2008 | Weaver et al. |
| 7,771,457 | B2 * | 8/2010 | Kay et al. ...................... 606/284 |
| 7,776,076 | B2 | 8/2010 | Grady et al. |
| 8,118,846 | B2 * | 2/2012 | Leither et al. ................. 606/280 |
| 2003/0199875 | A1 | 10/2003 | Mingozzi et al. |
| 2004/0193163 | A1 | 9/2004 | Orbay |
| 2005/0015089 | A1 | 1/2005 | Young et al. |
| 2005/0107795 | A1 | 5/2005 | Morris et al. |
| 2005/0192577 | A1 * | 9/2005 | Mosca et al. ................... 606/69 |
| 2005/0216008 | A1 | 9/2005 | Zwirnmann et al. |
| 2006/0129151 | A1 | 6/2006 | Allen et al. |
| 2006/0161158 | A1 | 7/2006 | Orbay et al. |
| 2006/0173458 | A1 | 8/2006 | Forstein et al. |
| 2006/0173459 | A1 | 8/2006 | Kay et al. |
| 2006/0200145 | A1 | 9/2006 | Kay et al. |
| 2006/0212035 | A1 | 9/2006 | Wotton, III |
| 2006/0235411 | A1 | 10/2006 | Blain et al. |
| 2006/0241608 | A1 | 10/2006 | Myerson et al. |
| 2007/0043366 | A1 | 2/2007 | Pfefferle et al. |
| 2007/0073298 | A1 | 3/2007 | Beutter et al. |
| 2007/0123883 | A1 | 5/2007 | Ellis et al. |
| 2007/0173840 | A1 | 7/2007 | Huebner |
| 2007/0185493 | A1 | 8/2007 | Feibel et al. |
| 2007/0233106 | A1 | 10/2007 | Horan et al. |
| 2007/0233112 | A1 | 10/2007 | Orbay et al. |
| 2007/0270850 | A1 | 11/2007 | Geissler |
| 2008/0051786 | A1 | 2/2008 | Jensen |
| 2008/0300632 | A1 | 12/2008 | Butler et al. |
| 2008/0300637 | A1 | 12/2008 | Austin et al. |

FOREIGN PATENT DOCUMENTS

| | | |
|---|---|---|
| EP | 1468655 A2 | 10/2004 |
| FR | 2233973 A1 | 2/1975 |
| FR | 2405062 A1 | 6/1979 |
| FR | 2405705 A1 | 6/1979 |
| FR | 2405706 A1 | 6/1979 |
| JP | 11299804 | 11/1992 |
| WO | 02096309 A1 | 12/2002 |
| WO | 2004086990 A1 | 10/2004 |
| WO | WO 2004086990 A1 * | 10/2004 |
| WO | 2008064211 A1 | 5/2008 |

OTHER PUBLICATIONS 3.5 mm LCP Superior Anterior Clavicle Plates. Part of the Small Fragment Locking Compression Plate (LCP) System by SYNTHES(R), Technique guide brochure, 24 pages, Sep. 2008.

Clavicle Locking Plate by Smith & Nephew PERI-LOC Locked Plating System, Brochure, 16 pages, May 2007.

Locking Bone Plate System for Hallux Valgus corrections "Opening or Closing Base Wedge" Osteotomy by MetaFix (TM) and merete(R), Brochure, 2 pages, Feb. 2005.

Dr. Michael Stephens, M.D., Hallu(R)-S Plate by Integra(TM), Pamphlet, 6 pages, Jan. 2005.

TOM(TM)-Platte by DARCO(R), Pamphlet, 2 pages, Dec. 8, 2006.

New Trauma Products from AO Development, Catalog, 2 pages, Jun. 2006.

Reconstructive Surgery, Integra(TM), Product Catalog, 4 pages including new deal(R), New ideas for foot surgery(TM), 2005.

* cited by examiner

ORTHOPEDIC PLATE FOR USE IN SMALL BONE REPAIR

CROSS-REFERENCE

This application is continuation application of pending U.S. patent application Ser. No. 13/348,888, filed on Jan. 12, 2012 for ORTHOPEDIC PLATES FOR USE IN CLAVICLE REPAIR AND METHODS FOR THEIR USE which is a divisional of U.S. Pat. No. 8,118,846, issued on Feb. 21, 2012 for ORTHOPEDIC PLATES FOR USE IN CLAVICLE REPAIR AND METHODS FOR THEIR USE which is a CIP of U.S. Pat. No. 7,771,457, issued on Aug. 10, 2010 for ORTHOPEDIC PLATE FOR USE IN SMALL BONE REPAIR which claimed priority to U.S. Provisional Application Ser. No. 60/648,364 filed on Jan. 28, 2005 for ORTHOPEDIC PLATE FOR USE IN SMALL BONE REPAIR.

FIELD OF THE INVENTION

The present invention relates to orthopedic plates in particular for surgical repairs or reconstruction of a clavicle and to a method for the use of these plates.

BACKGROUND OF THE INVENTION

The field of orthopedic medicine has grown tremendously in the past fifty years as surgical techniques, implants and instrumentation have developed and been improved. The small bones are frequently subject to the need for re-constructive surgery for example, as a result of trauma, to counteract the effects of aging or to repair congenital deformities and trauma and spinal areas. While there is a wide variety in the exact shape and mass of all bones, these variations become more problematic in providing orthopedic implants for small bone applications since there is less room on and about the bone for the surgeon to place and fix the construct. These bones are finer and have less surface area for placement of an implant, have less mass for the placement of screws and are often surrounded by less muscle and by more vulnerable tendons, blood vessels and nerves. As a result, individual variations become more problematic for orthopedic plates of stock design. Consequently, surgeons have tended to rely on the use of screws and wires for reconstruction or have had to resort to operating room contouring procedures which can weaken the plates and/or distort the screw holes within the plates. This is a particular problem in instances in which either variable locking mechanisms are used, or in which locking screws are used with the plates. None-the-less, locking screws often are used to advantage as they provide more secure placement of the screws in the bone, cause better compression through a fractures, and are less likely to harm the bone or back out of the plate.

One problem that needs to be avoided in the delicate environment of the small bone area is the interference of screws, with other screws, and with the function of ligaments and tendons. While it may be desirable to design an orthopedic plate so that securing screws converge in order to cause compression or increase the pullout strength, it is difficult when a screw impinges on or conflicts with the desired placement of another screw. Some surgeons prefer bicortical fixation in which a screw is sized so that the distil end is secured in cortical bone giving the screw better purchase, however, other surgeons may prefer to avoid placing a screw so that it projects beyond the outer surface of the anchoring bone. These factors are complicated by the relative lack of soft tissue and the presence of ligaments and tendons in the small bone areas. Consequently, the less forgiving biological environment in which the small bone surgeon works requires greater procedural precision and calls for specialized implants and tools.

The present invention is designed to meet the specific needs of the small bone surgeon to facilitate effective and repeatable procedures which provide for ease of use and a range of function for this specific area of specialization. The present invention is specifically intended to provide for the treatment of fracture repair following trauma in an otherwise healthy individual where plates are used to maintain the integrity of the bones while they heal, although it is certainly possible that they may also be used for other surgeries such as reconstruction to correct congenital or age related deformation or issues that relate to prior mal-union of the bone following a prior injury.

The plates of the present invention are designed specifically for the repair or reconstruction of a clavicle, which is commonly called a "collarbone". The collarbones, like the cheekbones, are covered only by skin, and thus have a high correlation to the appearance of the individuals and serve in many cultures as a marker of beauty. These bones further serve to protect the brachial plexus and the medial nerve and blood vessels that are immediately internal to them. They also serve as a strut and the only skeletal connection between the arms and the torso, and they play a very sophisticated role in the functioning of the shoulder girdle, torso, scapular and arm kinesiology. The effect of misalignment and mal-union of clavicle fractures are only recently being examined from the viewpoint of the strength and stamina of the patient as it was previously viewed radiographically and therefore underestimated.

It has been reported that as many as 5% of all fractures seen in the admissions department of an emergency room are clavicle fractures, which occur most commonly between the proximal ⅔ and the distal ⅓ of the bone. The more common fracture (approximately 80% of clavicle fractures) occurs in the middle third of the clavicle with an upward displacement of the proximal fragment of the bone by the sternocleidomastoid muscle. The weight of the shoulder muscles and of the adductor muscles of the arm may add to the fragment displacement, causing the shoulder to droop. This type of fracture often occurs as a result of a fall on an outstretched hand or of a direct blow to the clavicle. The second most common fracture (which may account for 10-15% of clavicle fractures) occurs in the distal ⅓ of the clavicle. The causes of the fractures are similar to those for the mid-shaft fractures, but also commonly include blows to the shoulder region, such as occur in automobile collisions and particularly physical sports such as hockey, lacrosse and football. Medial fractures are often associated with very severe trauma that includes injury to the vital organs and other indications of co-morbidity.

It is often difficult to reduce and subsequently to maintain the reduction of clavicle fractures without surgical intervention, although both union and healing proceeds rapidly, usually with the result of a prominent callus, and in some cases of mal-union, with the possibility of medial cord nerve symptoms. In the past, non-surgical treatment has often involved immobilization of the associated limb, such as in a figure-of-eight bandage or a simple sling. In a study published in the Journal of Bone and Joint Surgery, 2006 (88:35-40), by McKee et al, *Deficits Following Non-operative Treatment of Displaced Mid-shaft Clavicle Fractures*, the authors in particular note that that there was a substantial loss of strength and endurance in clavicle fractures treated with a traditional sling approach, indicating substantial residual disability despite apparently adequate range of motion. This and other studies have led to increased concern about providing wider range of surgical options for internal stabilization of the clavicle. However, the problem remains that the shape and size of clavicles vary greatly and their visibility leaves little room for plates that do not generally accommodate this variation gracefully.

The present invention provides answers to the prior art issues by providing a variety of plates with varying footprints that share an elongate central trunk with a medial line (which is intended in this instance to include a curving line) that divides the plate in half laterally. The plate further has at least one pair of terminal asymmetrical arms that extend from the trunk at differing angles relative to the medial line and have differing lengths. The plates also have varying profiles (or contouring) in the z direction but again share a transverse curve along the medial line about the side which faces the bone. The plates also all exhibit bilateral asymmetry (meaning that the left half of the plate is not exactly the same as the right half of plate taken from the medial line) and they all achieve bi-planar screw fixation (meaning that the screws do not lie in a single plane). In addition, while the plates are pre-contoured, the plates are designed to facilitate three dimensional contouring (at least in the terminal arms) to accommodate individual variation in bone shape. The plates are configured to bend laterally, longitudinally, and to wrap or spiral about the longitudinal axis or medial line so that they can be molded to an optimal shape for small bone procedures. The plates are designed to provide optimal stabilization of fractures and osteotomies by providing multi-planar fixation that allows for better pull-out and limited axial loading to the bone. The plates are further designed to accelerate fusion success by reducing or eliminating torsional or twisting stresses to the bone segments during the healing process. In addition, when desired, the plates can be shaped so as to apply a compressive, or even a tensile, force, for example, along the longitudinal axis of a bone.

These plates are provided in a number of variations in a surgical tray, which include for example various lengths of the central trunk portion, which is provided with a line of screw holes centered along the medial line. Further the number of screw holes in the trunk can vary, and the type of holes can vary to include translation slots, compression slots, and locking and non-locking screw holes. Thus, the tray selection allows the surgeon to select his plate during surgery after opening the wound area and considering the plating needs. In addition, the tray includes plates of differing types for differing placement on the clavicles in a first embodiment of the clavicle plate of the present invention, a plate is provided for placement on the superior aspect of a clavicle, and in a second embodiment, a plate is provided for placement on the anterior/inferior aspect of a clavicle, and in a third embodiment, a plate is provided for placement on the lateral aspect of a clavicle.

All of the plates have an elongate central trunk portion including one or more screw holes which are optionally separated by a waist shaped linking portion along a longitudinal axis or the medial line and depending on the embodiment, the plate has one pair or two pairs of arms which are preferably terminal to the central trunk, and which include screw holes (i.e. one per arm) placed at an equal distance from the longitudinal axis but which diverge asymmetrically from the longitudinal axis to avoid conflicts in the screw placement of the paired arm, specifically, so that the screws of a set of arms avoid impinging on each other and further to provide multi-planar fixation at the plate terminus. The plate is curved about the inferior surface, (i.e. the surface which faces toward and which may, but does not have to fully contact the bone), with a curvature corresponding generally to the curvature of a bony surface. In most of the embodiments of the plate this contouring is the result of a blending of one or more series of radiuses so that the plate may comprise a portion of a cylinder, or portions of a cylinders, or in the event that the medial line also defines a longitudinal curve in the z axis, a portion of a torroid. The pair of arms continue this curvature to spiral or wrap around the bone like a small portion of a double helix (i.e., extending through an arc of less than about 50°). The screw holes within the arms are placed so that the angle of the longitudinal axis of the screws converge in the direction of the distil end of the screw. The screw holes are placed with the longitudinal axis perpendicular to a tangent to the top surface of the arm with the effect that the longitudinal axes of the screws converge in the direction of the distil end. The convergence of the screw holes increases the pull-out strength of the screws.

Further the screw holes are rounded and the corresponding mating heads of the screws are rounded and have a low profile so that the screws can be seated with their longitudinal axes at a variety of angles. Preferably, there is at least 20° of conical rotation, and more preferably 25°, and most preferably 30° of conical rotation of the screw axis in relation to the longitudinal axis of the screw hole (i.e. the longitudinal axis of the screw can be rotated through a conical shape about the axis of the screw hole where the apex of the cone describes an angle of 30°). Alternatively and in many cases, preferably, the screw holes can include internal threads which mate with external threads on the head of the screws to cause locking of the screws relative to the plate.

While the screws are at convergent angles, the screws typically do not in fact impinge on each other, or conflict in their placement since each of the arms of the plate in a pair form a different angle to the central trunk so that the longitudinal axis of the screws are offset from each other along the length of the plate. The radiused configuration of the plate is designed to increase operating room efficiency by facilitating commonly desirable shapes while maintaining the required strength and by permitting bending without deforming the screw holes. This results in making customization in anticipation or during surgery easier.

The surgical tray of the present invention further includes a variety of screws. The screws useful with the plate of the present invention are self-starting, self-tapping screws including the option of partial or full cannulation. The screws include a unique cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess that may be a hexagon, a torx shape, or a modification of a torx shape, i.e. a multilobe shape having from 3 to 12 lobes, and preferably having 4 to 8 rounded recesses or lobes. The recess can be of a constant size in the direction of the longitudinal axis, or can taper inward along the longitudinal axis of the screw toward the bottom of the recess. The screws have a low profile, head which is rounded at the junction of the head and the shaft, and also rounded from the maximum diameter toward the top surface or the proximal end relative to the insertion tip, which includes the torque driving recess. This rounded low profile head keeps the screw from having any sharp projecting edges which could provide an irritation to the tissue in the vicinity of the plate and further seats in the plate so that no more than 10% by volume of the screw head projects from the plate.

The instruments for use with the system are well-balanced and ergonomically designed with sufficiently long handles to place the surgeon's hands outside of the line of radiation and designed to reduce fatigue in the operating room.

Depending on the intended placement of the plate, the central trunk, and the plate itself includes a general topography (i.e. the contour in the z direction) designed to maximize the fit on a variety of shapes and sizes of clavicle while enabling, but reducing the need for individualized contouring. This topography includes a c-shape lateral curve in the superior and 4-hole anterior plates, a fishtail (i.e., having a broad curve in the direction of the bone-facing surface of the plate terminating in a short up-turned curve at the end of the plate) shape in the longer anterior plates. The lateral plate has an S-curve of the medial line in the direction of the width of the plate. The plate system of the present invention is thus designed to fit a range of needs of the surgeon operating on the clavicles to allow him or her to perfect a variety of techniques using a set of instruments and a customizable plate and screw construct.

DETAILED DESCRIPTION OF THE INVENTION

The plate 10 of the present invention is shown having a bilaterally asymmetric shape with either one or two pairs of legs extending from a central trunk portion 12 defining the longitudinal axis of the plate. As shown the trunk portion 12 includes two screw holes or slots 14 along the longitudinal axis. However, as can be seen from FIGS. 12 through 18 the plate can be presented in a version which has a plurality of screw holes, for example up to 8 or more. The number of screw holes in the trunk portion 12 will depend on the length of the plate, and may range from 0 to 8, and more preferably from 2 to 4. In one embodiment these holes are compression holes or translation slots. The compression holes 14 are preferably slotted or elongated and optionally may have a larger radius area 11 on each of the screw holes facing in the same direction, and a smaller radius area 13 in order to induce a compression toward the smaller radius end. The holes may also or alternatively have a shallow shoulder or lip 18 which descends toward the inferior surface of the plate to allow the plate to be set initially and subsequently to be slide into a different position as the screws are tightened down. This allows compression to be applied across the middle of the trunk section. The plates include a visual indicator of the direction of the compression, such as an arrow 17. Further, the screw holes can include annular rings of increased thickness in the vertical direction about through holes 14.

The through holes 14 in the trunk portion 12 have a longitudinal axis that is perpendicular to plane tangent to the top radius of the plate. The area linking the screw holes has a decreased width so as to define a waist area 26 that will bend laterally (or "curve") relative to the longitudinal axis and which will bend longitudinally to form a curved area in and out of the plane of the plate. This thinner area also facilitates twisting of the plate so as to allow the plate to spiral, or wrap around it longitudinal axis. The increased annular area around the through bores resists deformation when a bending device is used to apply a force to the plate through the screw holes.

Figure 1:
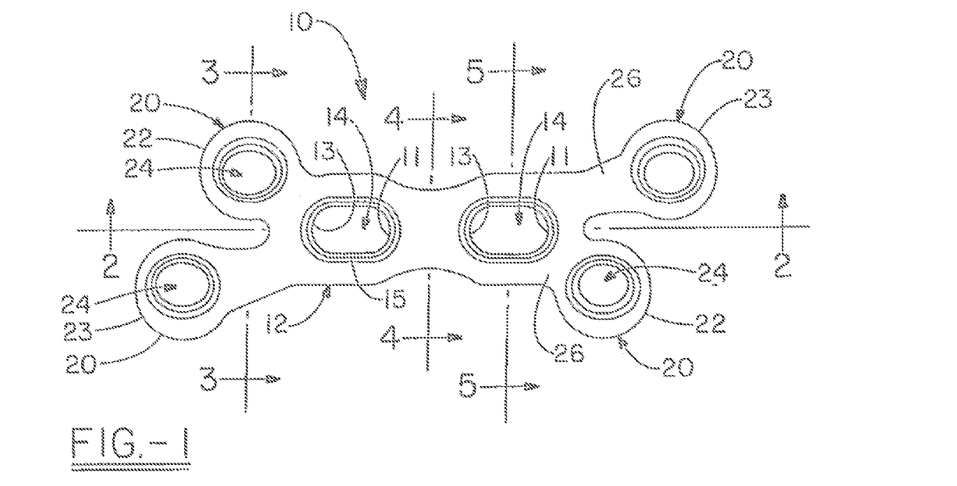
FIG. 1 is a top view of a first embodiment of an orthopedic plate in accordance with the invention.
Figure 2:
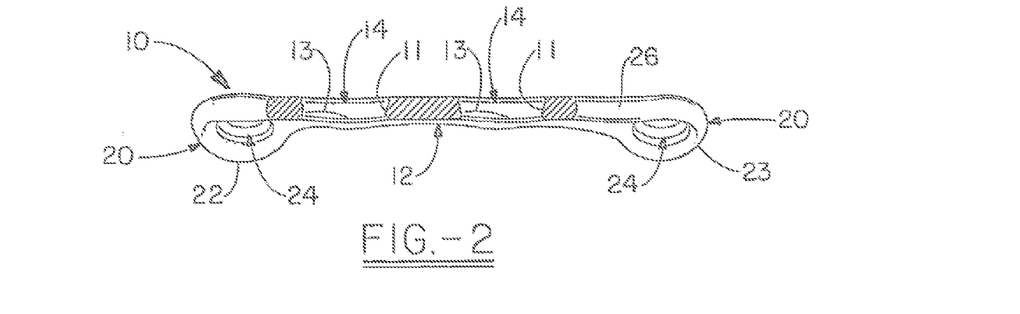
FIG. 2 is a cross-section of the plate of FIG. 1 taken along line 2-2.

The plate 10 also includes at least one set of arms 20. As viewed in FIG. 1, these sets of arms can be viewed as a set of a short 22 and a long arm 23. Each of the arms in a set includes screw holes 24 which are placed at a radially equal distance but which diverging asymmetrically from the longitudinal axis of the plate 10. More specifically, each set of arms includes one arm that defines a smaller angle of divergence $\alpha$ from the longitudinal axis of the trunk portion than the angle of divergence of the other arm $\beta$. For example, the first angle shown in FIG. 1 at $\alpha$ may be from about 5° to about to 25°, and more preferably from about 10° to about to 20° and most preferably from about 12° to about to 16°, while the second angle shown at $\beta$ from about 10° to about to 35°, and more preferably from about 15° to about to 30° and most preferably from about 22° to about to 26° with a preferred difference in the angles beings from about 2° to about to 20°, and more preferably from about 4° to about to 16° and most preferably from about 8° to about to 12°.

In addition to the angled arms of this asymmetrical shape facilitating a variety of useful positions in the small bone area, the plate of the present invention is sized to fit the needs of the small bone specialist. For small bone usage, the total length of the plate along its longitudinal axis is from about 25 mm to about 80 mm, depending on the number of screw holes in the trunk portion. The total width is from about 12 mm to about 18 mm, with an inferior radius of curvature of about 8 mm to about 12 mm and a concentric radius on the superior side. Typically, the waist area measures from about 7.5 mm to about 10 mm from the center of the larger, i.e. about 3.8 mm, radiused portion of the holes. The trunk portion has a width of about 7 mm to about 9 mm wide at the wider parts and about 3 mm to about 5 mm wide at the narrower waist portion. The longer arm has a length along the longitudinal axis of the plate from the center of the screw hole to the center of the plate for a two-hole trunk of from about 12 mm to about 16 mm, with a width of about 3 mm to about 5 mm. The shorter arm has a comparable length of from about 7 mm to about 15 mm with a narrowed width of about 2.5 to about 5 mm. In a further embodiment the plate could be modified for use in the long bones with a length of up to about 400 mm with a width of up to about 50 mm, and proportional sizes for the arms and thickness.

On the inferior side, or the side that would be facing (which contemplates opposing or touching or partially touching) the bone surface in use, the arms continue the radius of curvature of the trunk portion. The superior or top side of the plate has a similar radius of curvature as the top surface of the plate has an outline that corresponds with the shape of the bottom of the plate (excluding the optional thickened annular area surrounding the screw holes which would act to shield these holes against deformation during bending.) The screw holes also include a rounded concavity to mate with the rounded shape of the head of the screw to allow of variable axis positioning. The screw holes 24 are placed with the longitudinal axis perpendicular a tangent to the top surface of the arm with the effect that the longitudinal axes of the screws converge in the direction of the distil end. This increases the pull-out strength of the plate/screw construct. Since the arms are asymmetrical relative to each other, and in particular since they diverge from the longitudinal axis of the trunk portion at differing angles, conflicts in the positions of paired screws is avoided so that the screws of a set of arms typically do not impinge on each other. This is even more important in instances where the plate is bent around the longitudinal axis so as to wrap around the longitudinal axis of the bone.

The arms 20 also each include a screw hole 24 which, like the trunk portion 12 has a linking portion 26 that joins the screw hole to the trunk portion. Again this design facilitates the desired bending while resisting deformation of the screw holes 24 when they are used with the bending instrument to contour the plate. The angle of the arms 20 of each one of a pair of arms (both top and bottom and right and left pairs) varies so as to create a bilateral asymmetry, meaning that the plate is not symmetrical with respect to a plane that passes through the longitudinal axis in the vertical direction from the superior (the top side relative to the bone) to the inferior side (the side facing the bone), the "first plane".

Figure 3:
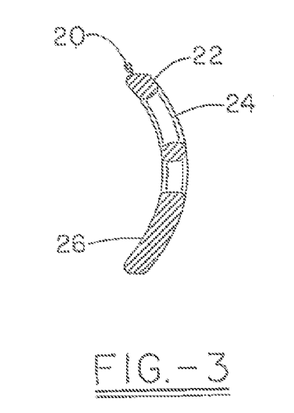
FIG. 3 is a cross-section of the plate of FIG. 1 taken along line 3-3.
Figure 4:
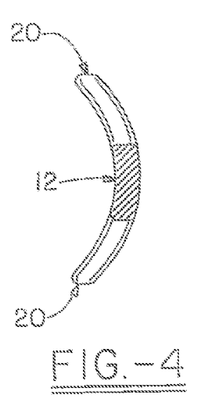
FIG. 4 is a cross-section of the plate of FIG. 1 taken along line 4-4.
Figure 5:
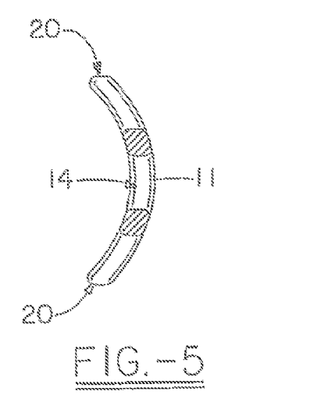
FIG. 5 is a cross section of the plate of FIG. 1 taken along line 5-5.

The screws holes of the trunk portion can include means to induce a compressive force in one direction, such as a ramped area on each screw hole. These ramped areas would be ramped on the same side of the holes looking down from the top of the plate. Typically the first screw implanted stabilizes and the second screw is used to achieve compression. Further the length of each of the arms of a pair will vary so that the radial length of the center of the screw hole to the intersection with the longitudinal axis will be the same. As shown in FIGS. 3-5, the plate includes a radial curve about the longitudinal axis. The radius is typically about 10 mm with a transverse dimension from the edge of one arm to the edge of the other arm of a pair being about 15 or 16 mm for typical small bone usage, and the screw bore having a longitudinal axis of about 24° to a plane passing through the longitudinal axis of the plate. The bores are typically about 3.75 mm for a 3.5 mm diameter screw for small bones excluding the smallest of applications which would include phalanges. Again, for the smallest application as well as long bone embodiments the screws and corresponding screw holes could be sized to range from a 1.5 mm diameter screw up to a 7.5 mm diameter screw. In a further embodiment, the bore could be threaded.

Figure 6:
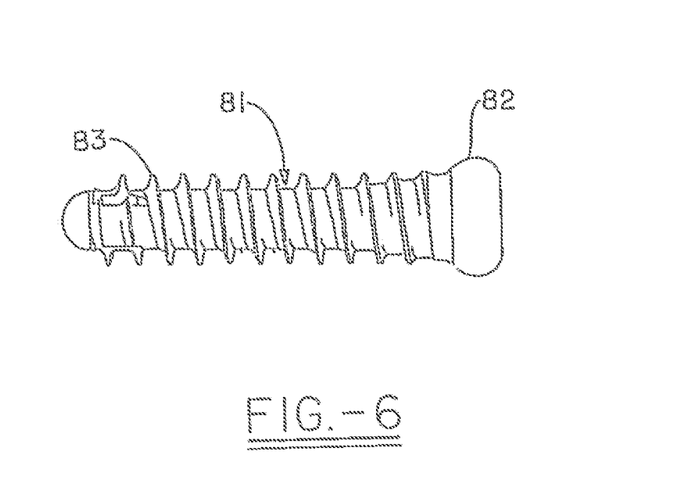
FIG. 6 is a perspective view of a screw used with the present system.
Figure 7:
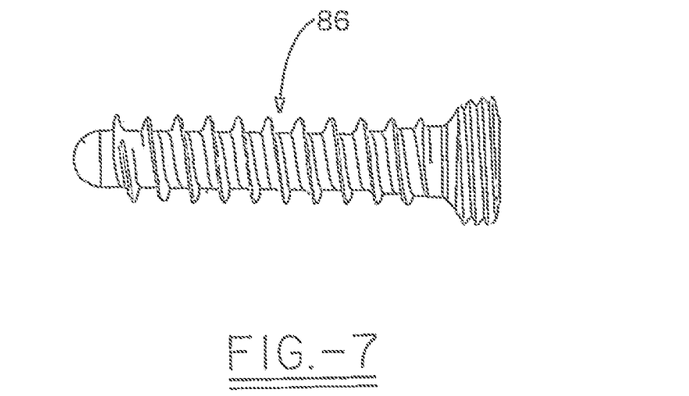
FIG. 7 is a perspective view of a locking screw used with the present invention.

FIG. 6 shows a screw 81 which could be used with the plate system of the present invention. The distil end of the screw can include a cutting tip which is self-starting and self-tapping or a rounded blunt tip. This aspect is defined by a conical recess and a plurality of flutes. These screws 81 can optionally include partial or full cannulation. The head of the screw 82 is spherical and includes a torque driving recess, such as a modified multilobe shape. The screw has a cancelleous thread 83 with a constant major diameter and a minor diameter that tapers proximally in order to increase fatigue life of the screw and to improve compression and compensate for bone resorption. FIG. 7 shows a locking screw 86 which could be used with the present invention. The screw includes the same features as the screw in FIG. 6, except that the screw further includes external threads 88 on the screw head.

Figure 8:
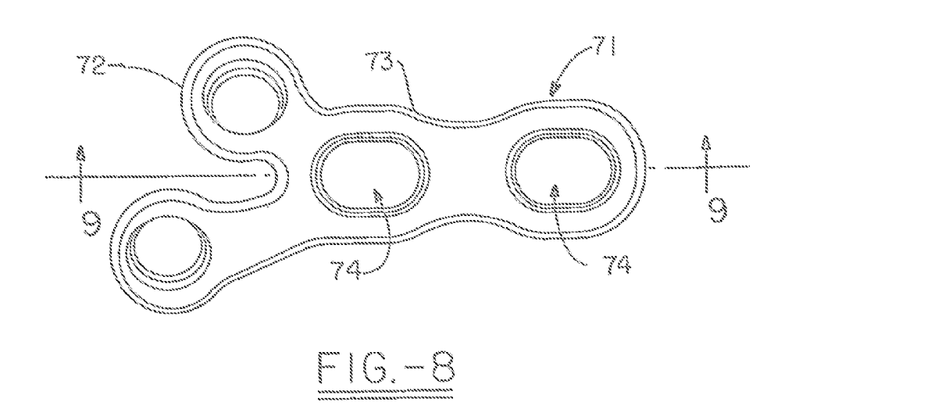
FIG. 8 is a top view of a first version of a second embodiment of the plate in accordance with the invention.
Figure 9:
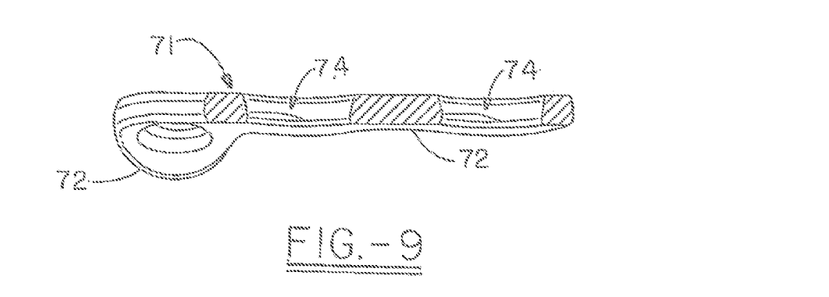
FIG. 9 is a cross section of the plate of FIG. 8 taken along line 9-9.
Figure 10:
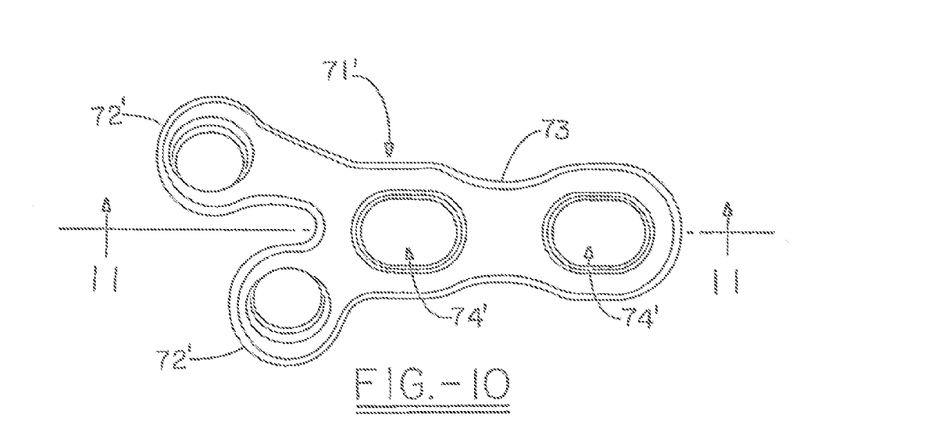
FIG. 10 is a mirror version of the plate shown in FIG. 8.
Figure 11:
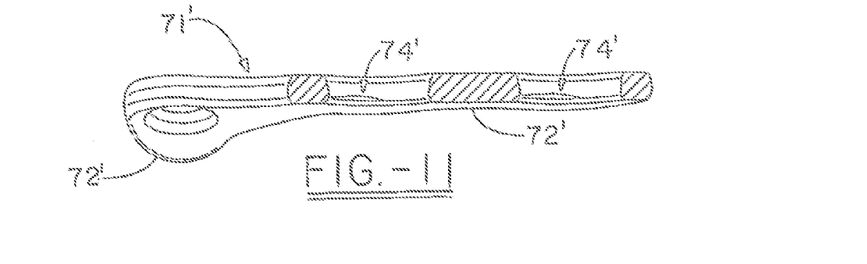
FIG. 11 is a cross section of the plate of FIG. 10 taken along line 10-10.
Figures 12, 13:
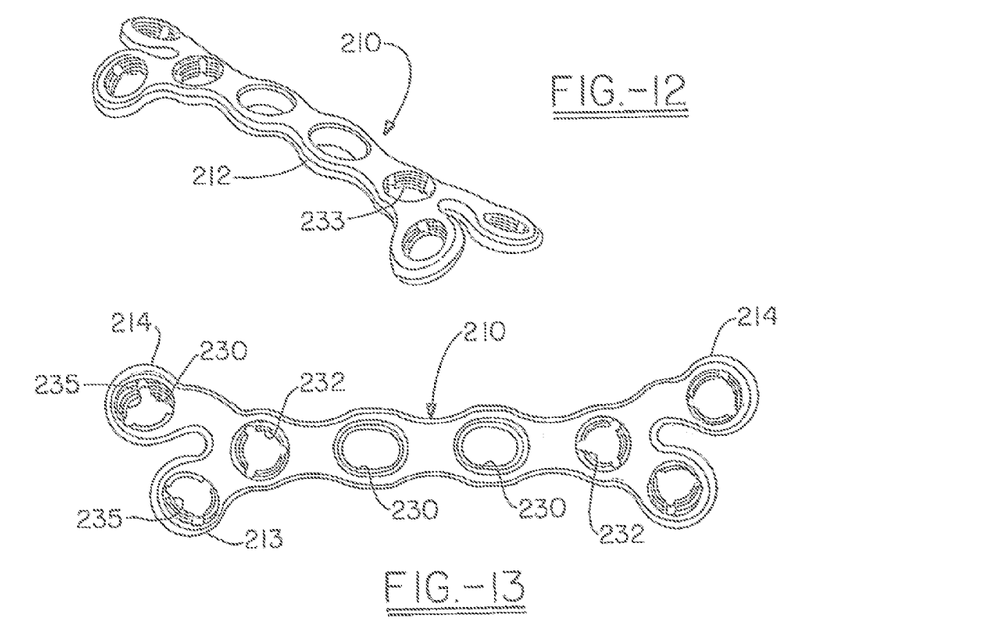
FIG. 12 is an and perspective of a left version of a third embodiment of a plate in accordance with the invention for placement on the anterior aspect of a clavicle.
FIG. 13 is a top view of the plate of FIG. 12.
Figure 14:
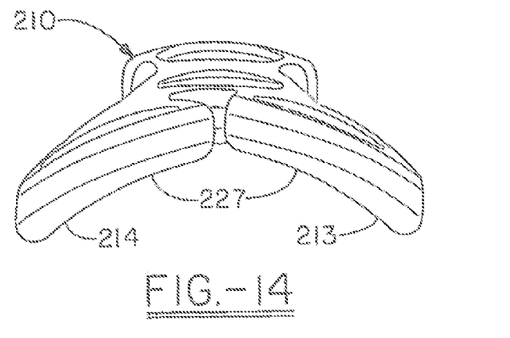
FIG. 14 is a right end view of the plate of FIG. 12.
Figure 15:
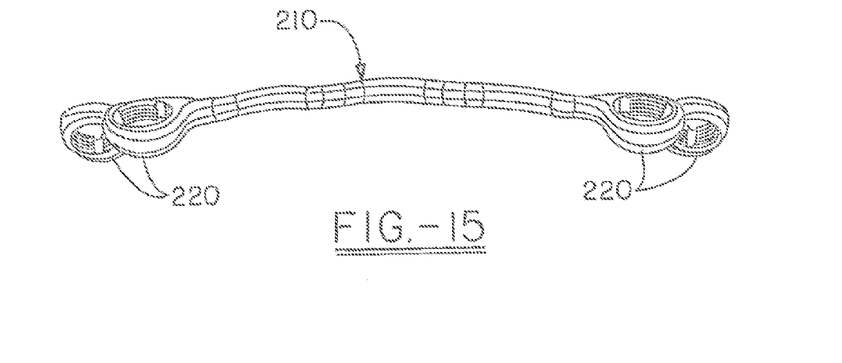
FIG. 15 is a right side view of the plate of FIG. 12.
Figure 16:
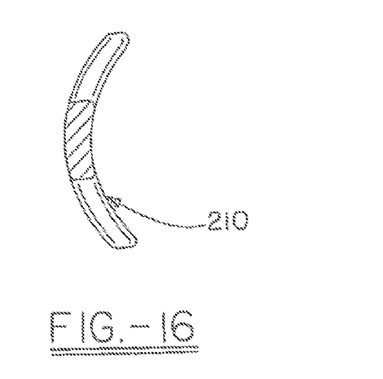
FIG. 16 is a cross section of the plate of FIG. 12 taken across the width of the plate.

FIGS. 8 through 11 show a second embodiment of a plate in accordance with the present invention in which the plate shown in FIG. 10 is a mirror image of the plate shown in FIG. 8. In this embodiment, the plate 71, 71' has a Y-shape with an elongate and cylindrical central trunk having a single pair of arms 72, 72' extending as previously described from the a trunk portion 73, 73'. The trunk portion optionally has one or more compression slots 74,74'.

FIGS. 12 through 17 show an embodiment of the present invention for placement on an anterior aspect of a left clavicle with the version for the right clavicle being a mirror image. This embodiment of the plate 210 has a profile having a central trunk 212 with two sets of terminal arms 220 similar to the plates shown in FIGS. 1-5 except that the short arms extend away from the same side of the trunk relative to the medial one. Thus, the plate forms an X with two short arms 213 on the same side and two longs arms 214 on the same side and the elongate central trunk 212 bridging the span between each terminal set of arms. The central trunk includes a slight longitudinal curve, and the bottom 227 of the plate has a radial curve as can be seen in the end view of FIG. 14, and in the cross-section shown in FIG. 16. Thus, the plate forms a segment of a torroid. The trunk includes two translation slots 230, which are obround and in the middle of the plate and which are used for initial fixation and which subsequently allow for translation of the plate relative to that fixation. The plate further includes two screw holes 232 which are shown as locking holes having internal threads. These holes further include keyways 233 for the mating portion of a drill guide in order to set the pilot hole for a locking screw received in these holes.

The plate 210 has a two pairs of arms 220 that extend as previously described. Specifically, for each pair of arms, each of the first 213 and second arm 214 include a screw hole 235 which defines an axis of the screw (perpendicular to a tangent at the diameter of the screw hole) and the arms have a longitudinal axis which is a line intersecting the screw axis and the longitudinal axis of the central trunk. The arms spiral or wrap around in the same direction that the central trunk does. The screw holes 235 are preferably threaded locking holes, which also include keyways for a drill guide that sets the angle for the locking screw. For each arm, the longitudinal axis defines an angle relative to the longitudinal axis of the central trunk, and the angle is different for one arm than for the other arm in a terminal pair as is shown for the embodiment shown in FIG. 1. The plate demonstrates a mirror symmetry about the transverse plane since the two short arms have a corresponding angle, length and shape and the two long arms have a corresponding angle, length and shape.

Figures 17, 18:
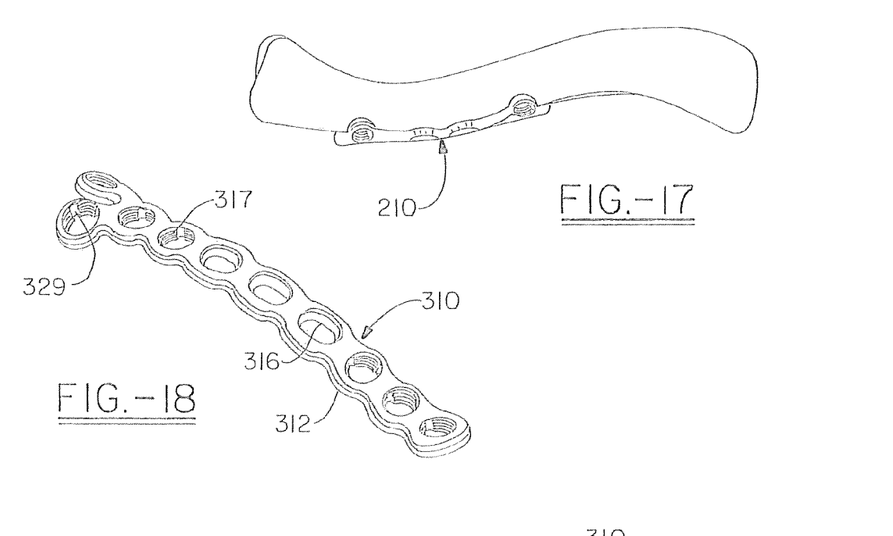
FIG. 17 is view of the plate of FIG. 12 placed on a clavicle.
FIG. 18 is an end perspective of a left version of a fourth embodiment of a plate in accordance with the invention for placement on the anterior aspect of a clavicle.

As has been previously described, the pair of arms include an inferior curve in the same direction as the radial curve in the central trunk portion. The difference in the length and angles of the arms allows for multiplanar fixation and convergence of the screws (which are locking screws) while avoiding impingement of the screws with each other. Thus, the plate is designed to fit the lateral ⅔ of the clavicle and the arms are designed wrap around the shaft of the bone. The plate is shown with a central trunk that includes two obround slots in the central trunk and two locking screw holes that include internal threads and keyways for a drill guide to set the angles for the screws. The plate also includes two terminal sets of arms each having a short arm and a long arm with the short arms on the same side for ease of insertion through the incision. The plate can have one or no slots and from 1 to 8 screw holes. FIG. 17 illustrates the placement of the plate on the anterior/inferior aspect in the mid-shaft portion of a clavicle.

FIGS. 18-29 show two slightly different embodiments of the plate of the present invention which vary according to the length of the elongate central trunk and accordingly, to the number of screw holes in this section of the plate. However, in both versions, the plate 310, 310' has a y-shaped footprint which comprises an elongate central trunk 312, 312' having a medial line and along the medial line, through holes, (which can either be slots 316, 316' such as compression slots or translation slots) and/or screw holes 317, 317' (which can either be smooth for variable locking or threaded for locking holes). In these embodiments, the holes of the central body are aligned with their centers along a straight medial line (or in this instance a plane), which divides the plates in two lateral halves. The area between the through holes curves inward toward the medial line to allow the plate to be further contoured without deforming the holes.

Figures 19, 20:
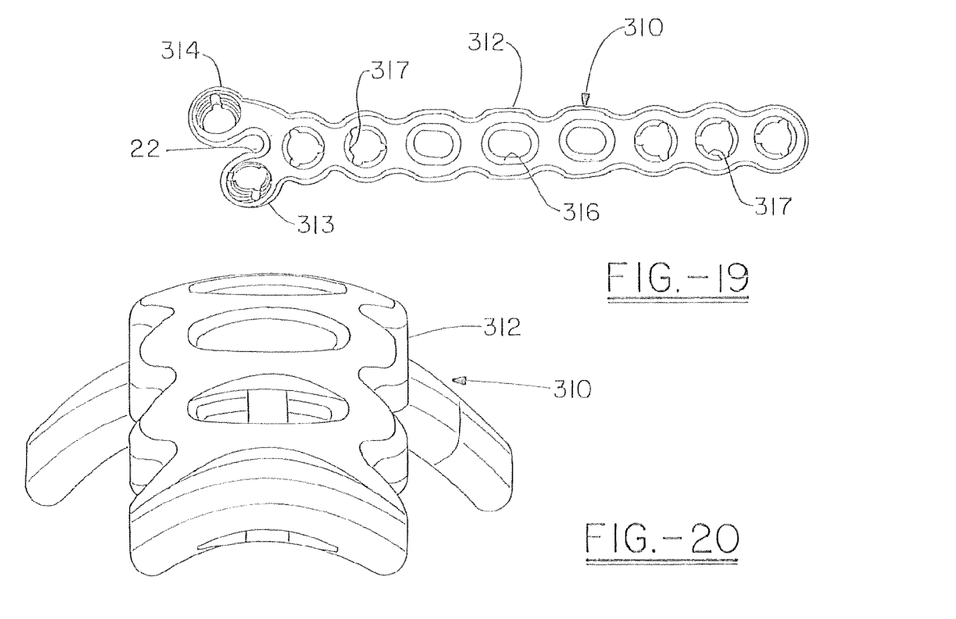
FIG. 19 is a top view of the plate of FIG. 18.
FIG. 20 is a right end view of the plate of FIG. 18.
Figure 21:
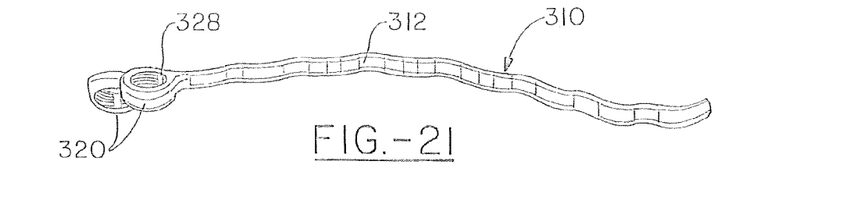
FIG. 21 is a right side view of the plate of FIG. 18.
Figure 22:
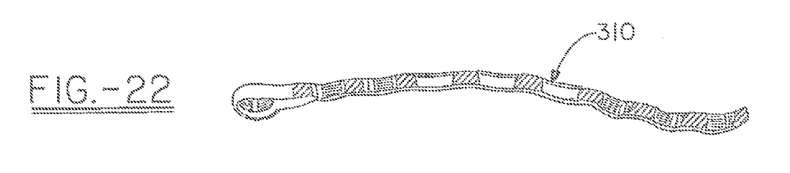
FIG. 22 is a cross section of the plate of FIG. 18 taken along line 22-22.
Figure 23:
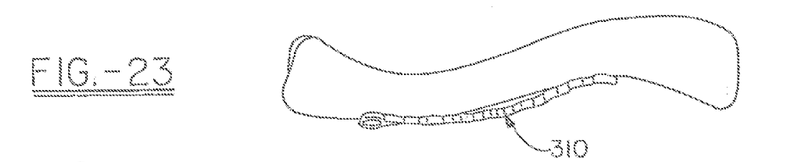
FIG. 23 is view of the plate of FIG. 18 placed on a clavicle.
Figure 24:
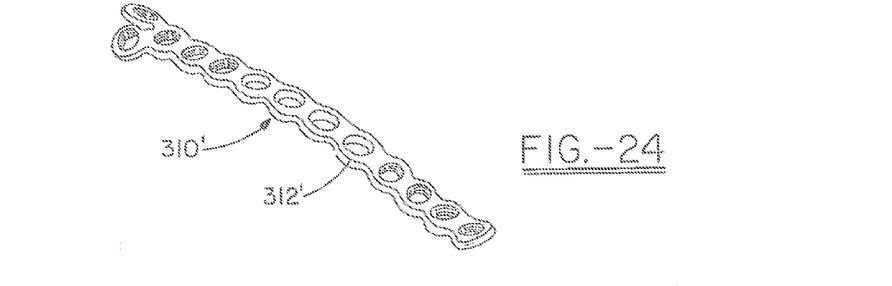
FIG. 24 is a top view of a left version of a fifth embodiment of a plate in accordance with the invention for placement on the anterior aspect of a clavicle.
Figure 25:
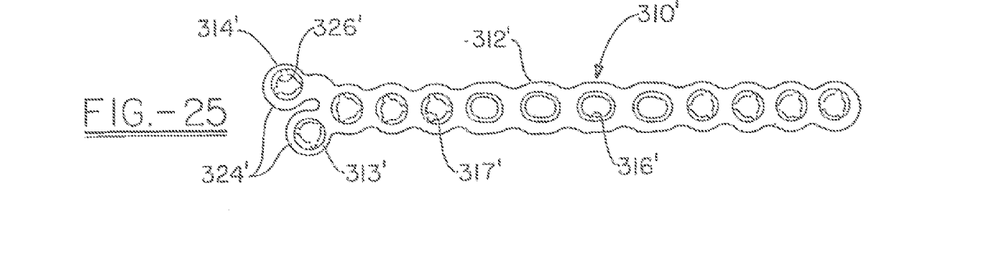
FIG. 25 is an end perspective of the plate of FIG. 24.
Figure 26:
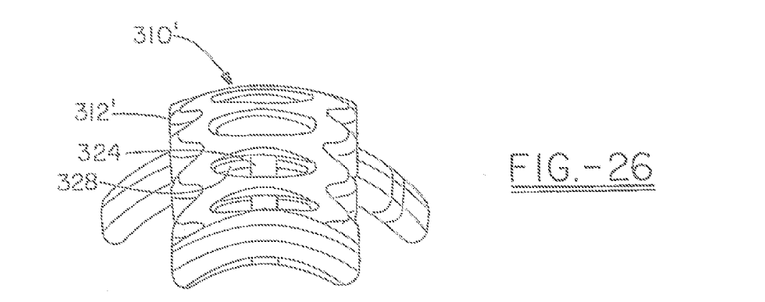
FIG. 26 is a right end view of the plate of FIG. 24.
Figure 27:
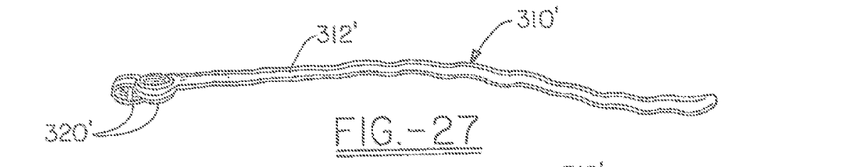
FIG. 27 is a right side view of the plate of FIG. 24.
Figure 28:
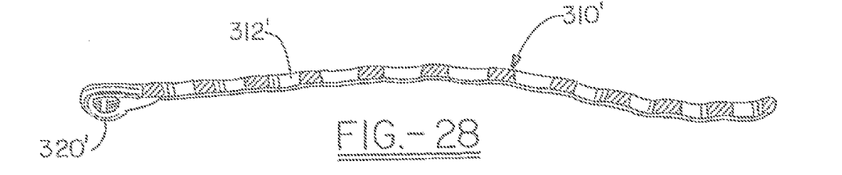
FIG. 28 is a cross section of the plate of FIG. 24 taken along line 28-28.
Figures 29, 30:
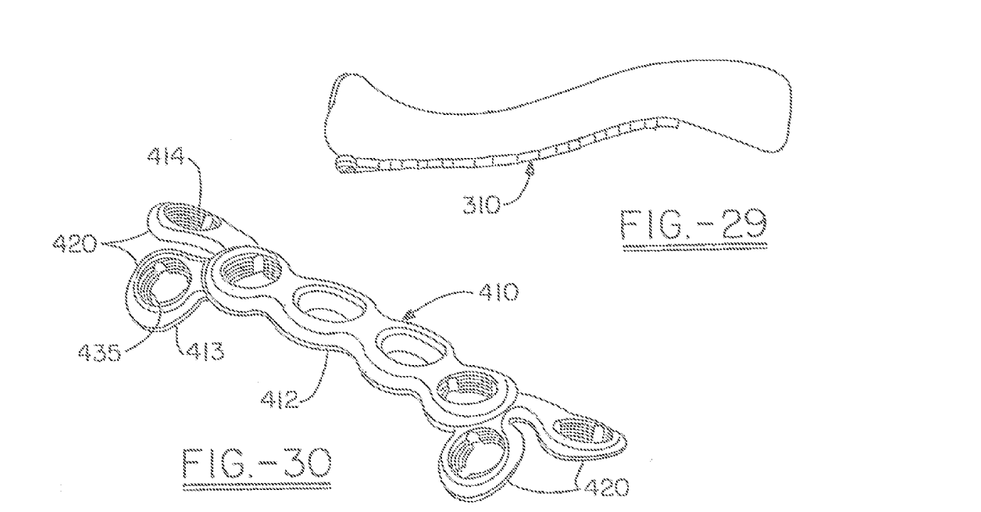
FIG. 29 is view of the plate of FIG. 24 placed on a clavicle.
FIG. 30 is an end perspective of a left version of a sixth embodiment of a plate in accordance with the invention for placement on the superior aspect of a clavicle.
Figures 31, 32:
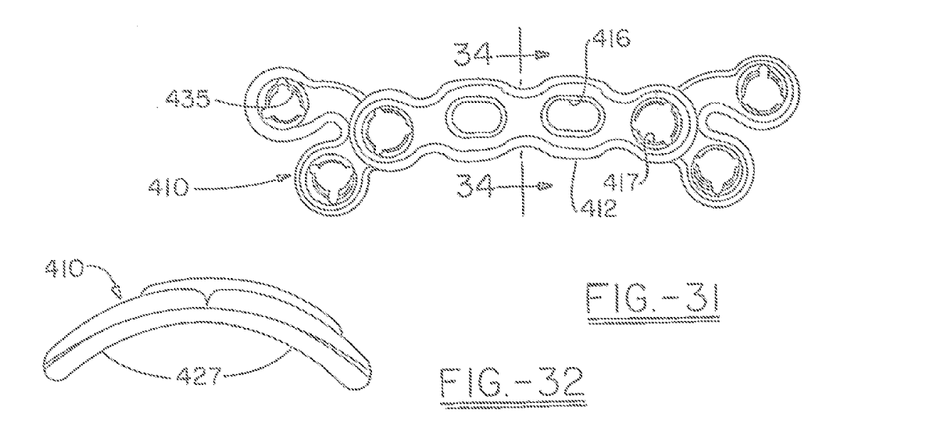
FIG. 31 is a top view of the plate of FIG. 30.
FIG. 32 is a right end view of the plate of FIG. 30.
Figure 33:
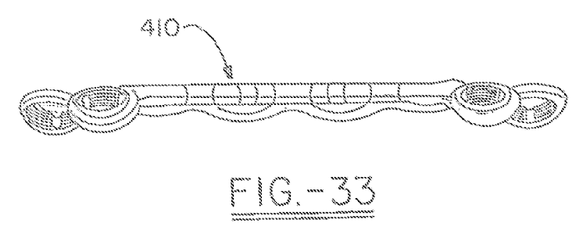
FIG. 33 is a right side view of the plate of FIG. 31.
Figure 34:
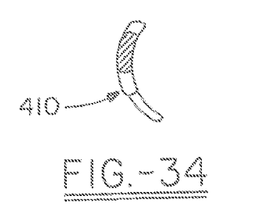
FIG. 34 is a cross section of the plate of FIG. 30 taken along line 34-34.
Figures 35, 36, 38:
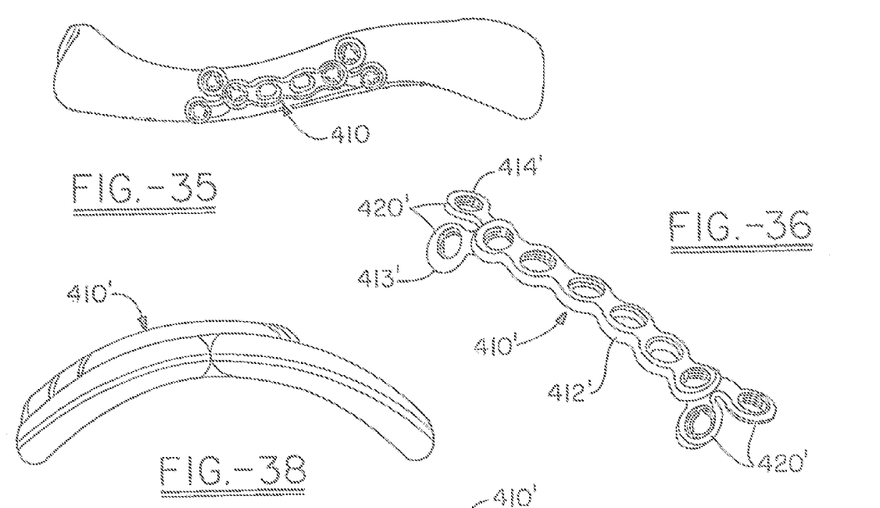
FIG. 35 is view of the plate of FIG. 30 placed on a clavicle.
FIG. 36 is an end perspective of a left version of a seventh embodiment of a plate in accordance with the invention for placement on the superior aspect of a clavicle.
FIG. 38 is a right end view of the plate of FIG. 36.
Figure 37:
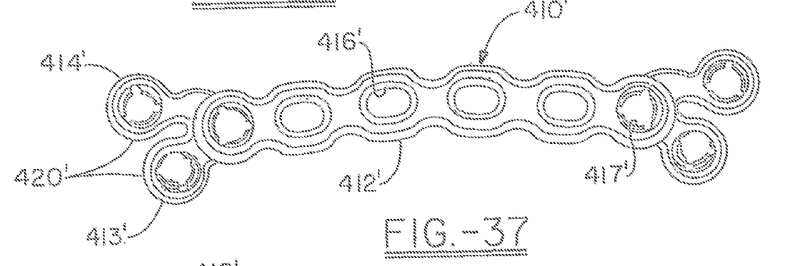
FIG. 37 is a top view of the plate of FIG. 36.
Figure 39:
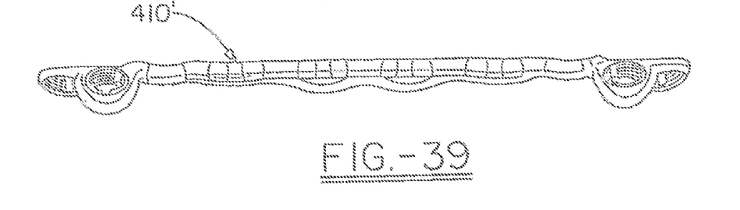
FIG. 39 is a right side view of the plate of FIG. 36.
Figures 40, 41, 42, 43, 44:
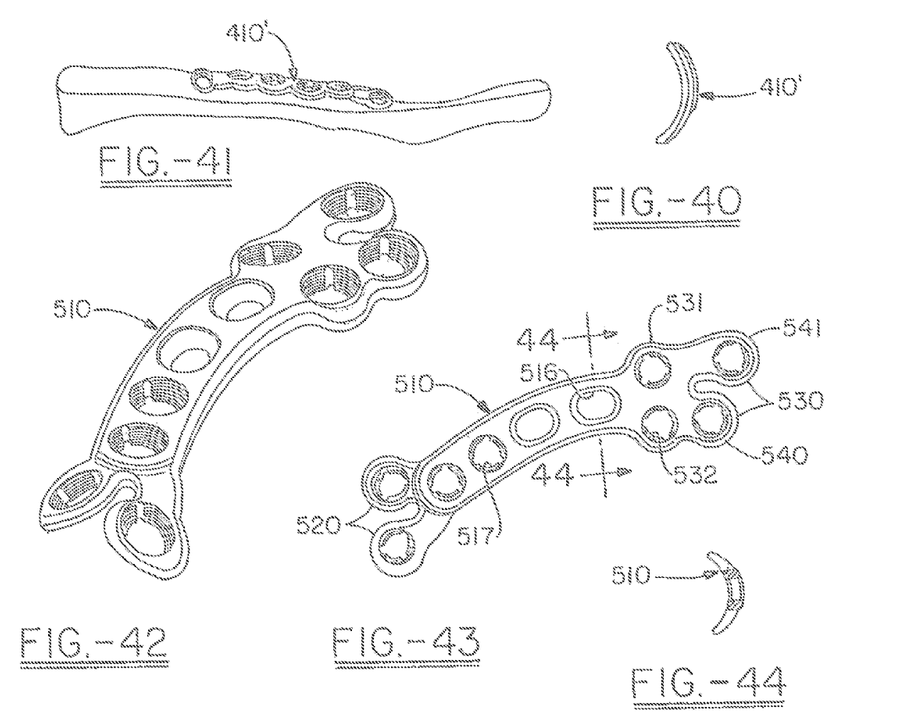
FIG. 40 is a cross section of the plate of FIG. 36 taken along line 40-40.
FIG. 41 is view of the plate of FIG. 36 placed on a clavicle.
FIG. 42 is an end perspective of a left version of an eighth embodiment of a plate in accordance with the invention for placement on the lateral aspect of a clavicle.
FIG. 43 is a top view of the plate of FIG. 42.
FIG. 44 right end view of the plate of FIG. 42.
Figure 45:
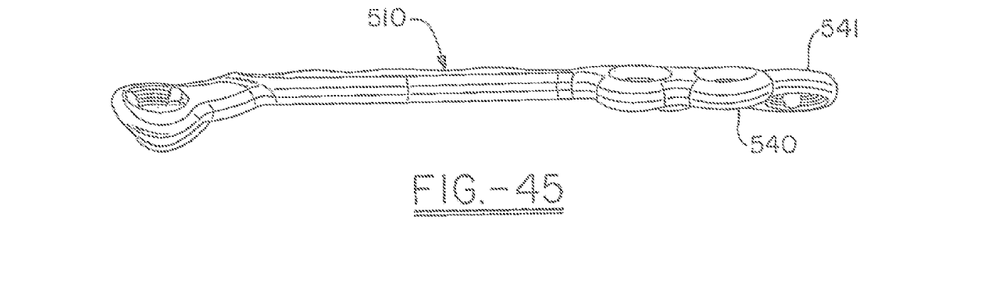
FIG. 45 is a right side view of the plate of FIG. 42.
Figure 46:
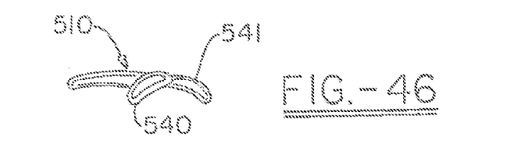
FIG. 46 is an right end view of the plate of FIG. 42.

One end of the central trunk includes a single pair of arms 320, 320' with a longer arm extending at a first angle from the medial line of the plate and having a shorter length than the second arm which extends from the plate at a second angle and has a longer length. The arms include a rounded portion 324, 324' that defines a portion of a circle and has a linking area that has a smaller width than the diameter of the circle. Each rounded portion includes a screw hole 326, 326' may advantageously include internal threads 328, 328' and keyway grooves 329, 329' for a drill guide. These embodiments of the plates are provided in a first version having five locking holes 317, in the central trunk and three obround translation slots 316. The translation slots 316 may include contouring with in the lateral edges of the slot that are convex to receive the rear shoulder or rounded portion of the screw in order to cause the screw to seat in the plate perpendicularly to the medial line. The plate is provided in a right and a left version and the left version is illustrated in the figures. In this version, the plate is curved along the medial line transverse to the medial line as can be seen in FIGS. 20 and 22. The plate also includes a larger contouring which is like the shape of a fishtail in that it bows gently from the end with the pair of arms in a first direction for approximately the first ¾ to 9/10 of the length of the plate, and then curves more sharply in the opposite direction along the z axis.

In the longer version of this plate 310', the plate includes four obround translation slots 316' which are in the center between three locking screw holes 317' at the end with the arm 320' and four locking screw holes 317' at the other end of the central trunk. This plate has similar contouring to the shorter version of this plate, with a radius on the bottom and a fishtail curve with a longer, and shallower curve which defines a curve that bows in a first direction from the arms through the second of the second set of locking holes, and the plate including the last two locking holes defines a curve in the opposite direction. Both of these plates are designed for placement on the middle portion of a clavicle and the choice between the two versions depends on the placement and nature of the fracture involved.

FIGS. 30 through 41 illustrate plates that are intended for use on the superior aspect of the clavicle. Again, left versions are shown, with the right version being mirror images of the left version. These plates 410, 410' have elongate central trunk portions 412, 412' with two opposing pairs of arms 420, 420'. Each of the first 413, 413' and second arm 414, 414' of a pair of arms 420, 420' include a screw hole 435, 435' which defines an axis of the screw (perpendicular to a tangent at the diameter of the screw hole) and the arms have a longitudinal axis which is a line intersecting the screw axis and the longitudinal axis of the central trunk as medial as possible to the arm. The arms spiral or wrap around in the same direction that the central trunk does. The screw holes 435, 435' are preferably threaded locking holes, which also include keyways for a drill guide that sets the angle for the locking screw. For each arm, the longitudinal axis defines an angle relative to the longitudinal axis of the central trunk, and the angle is different for one aim than for the other arm as is shown for the embodiment shown in FIG. 1. The plates demonstrates a mirror symmetry about the transverse plane since the two short arms have a corresponding angle, length and shape and the two long arms have a corresponding angle, length and shape.

The central trunk in the two versions shown in FIGS. 30-41, (with the shorter version shown in FIGS. 30-35 and the longer version shown in FIGS. 36-41) varies by the length and accordingly by the number of through holes in the trunk. In the shorter version, there are two translation slots 416 that are aligned along the medial line and are flanked by a first locking screw hole 417 and a last locking screw hole 417. This area of the plate also includes curves between the screw hole that allow the plate to be contoured without bending the through holes. The plate had a shallow longitudinal C curve in the direction away from the shorter arm side of the plate. The bottom side 427 of the plate also includes a radius to better accommodate the shape of the bone.

The version of the plate shown in FIGS. 36-41 has a longer central trunk 412' which includes four translation slots 416' aligned along the medial line and flanked by two locking screw holes 417'. Again, the central trunk portion of the plate curves gently in the direction of the shorter arms and the bottom 427' of the plate includes a radius. FIG. 35 shows the placement of the shorter plate on the inferior spine of a clavicle.

Figure 47:
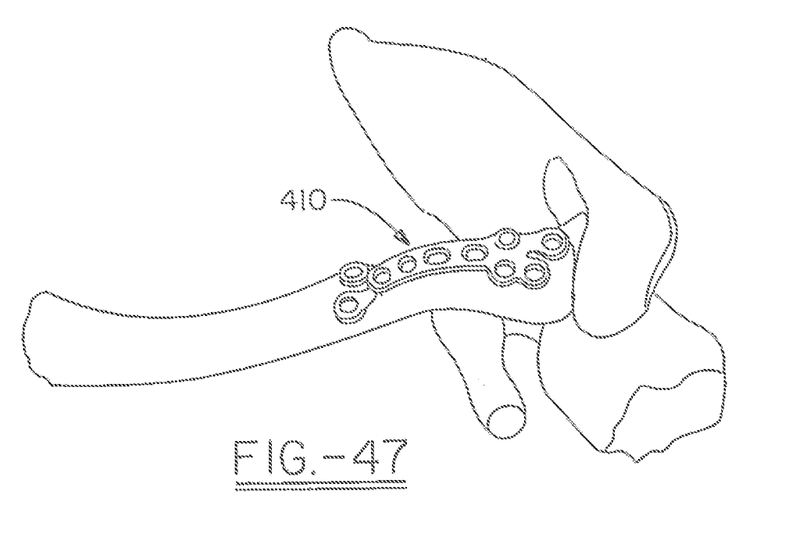
FIG. 47 is a view of the plate of FIG. 42 placed on a clavicle.

FIGS. 43-47 illustrate a plate for use on the lateral aspect of the clavicle. This plate 510 has an x-shaped profile, with an elongate central trunk and a first pair of arms 520 which extend at different angles and for different lengths from the trunk and further which include a curve on the bottom side so that the arms spiral around the bone and the screws that are placed in screw holes 535 in the arms provide for multiplanar fixation and do not impinge on each other. The central trunk includes two translation slots 516 and two locking screw holes 517 in the proximal end of the plate (i.e. adjacent to the end with the pair of arms 520). The other end of the plate includes a pair of arms 530 that differs from the other pairs in that there is a necked transition area 531 including screw holes 532 that are aligned with the terminal screw holes 533 in these arms. There is again a shorter arm 540 and a longer arm 541, which include threaded locking screw holes and keyway guide grooves. The plate has a shallow S shape along the medial line with the more proximal of the two translation slots marking the transition between the lobes of the S. The plate includes a bottom radius. FIG. 47 shows the plate in position on the distal portion of a clavicle.

While in accordance with the patent statutes, the best mode and preferred embodiment have been set forth, the scope of the invention is not limited thereto, but rather by the scope of the attached claims.

What is claimed is:

1. A surgical plate comprising:
   a pre-contoured Y-shaped plate having an inferior surface and a superior surface, the plate consisting of a trunk and pair of a first arm and a second arm,
   the trunk having a linear medial longitudinal axis along the superior surface extending between a first and a second end;
   the first arm having a first arm linear medial axis and an ear with at least one screw hole defining a first screw axis and which is a threaded locking screw hole, the first ear being attached directly to the trunk by a linking section having a waist, a first angle being defined by an intersection of the medial longitudinal axis of the trunk with the first arm linear medial axis, and a first length being defined by a line from a center of the first arm screw hole along the first arm linear medial axis to the medial longitudinal axis of the trunk, and,
   the second arm having a second arm linear medial axis and a second ear with at least one second screw hole defining a second screw axis and which is a threaded locking screw hole, the second ear being directly attached to the trunk by a linking section having a waist, a second angle being defined by an intersection of the medial longitudinal axis of the trunk with the second arm linear medial axis, and a second length being defined by a line from a center of the second arm screw hole along the second arm linear medial axis to the medial longitudinal axis of the trunk, and the first angle and the first length being different from the second angle and the second length whereby the first screw axis and the second screw axis converge toward the inferior side of the plate but do not intersect and wherein the first screw hole and the second screw hole are placed a radially equal distance from the medial line of the elongate central trunk.

2. The surgical plate as set forth in claim 1, wherein the intersection of the medial longitudinal axis of the trunk with the first arm linear medial axis is the same intersection as the intersection of the medial longitudinal axis of the trunk with the second arm linear medial axis.

3. The surgical plate as set forth in claim 2, wherein the intersection of the first arm and the intersection of the second arm are the same intersection.

4. A surgical plate as set forth in claim 1, further including a first locking screw and a second locking screw and wherein each of the first locking screw and the second locking screw have a proximal end and a distal end which extends from the plate, and the distal ends of the screws converge toward each other, but do not impinge.

5. A surgical plate as set forth in claim 4, wherein one or both of the first locking screw and the second locking screw are variable locking screws.

6. The surgical plate as set forth in claim 1, wherein the plate defines a medial line and the plate is bilaterally asymmetrical about the medial line.

7. The surgical plate as set forth in claim 1, wherein the plate defines a transverse axis and the plate is bilaterally asymmetrical about the transverse axis.

8. The plate system as set forth in claim 1, wherein the plate defines a transverse axis and the plate has mirror symmetry about the transverse axis.

9. The surgical plate as set forth in claim 1, wherein the plate has only one set of arms and an outline that forms a Y-shape.

10. The surgical plate as set forth in claim 1, wherein the plate defines a medial line and the trunk has an inferior surface defining a curve transverse to the medial line.

11. The surgical plate as set forth in claim 10, wherein the curve is constant along the medial line.

12. The surgical plate as set forth in claim 11, wherein the curve is a portion of a circle and the plate defines a segment of a cylinder.

13. The surgical plate as set forth in claim 1, wherein each arm includes a linking section joining the arms to the trunk and each linking section has a waist.

14. The surgical plate as set forth in claim 13, wherein the waist of the linking section of the first arm and of the second arm is configured to bend relative to the trunk in response to a force applied to at least one of before or during surgery without deforming the threaded screw hole of that arm.

15. The surgical plate as set forth in claim 1, wherein the trunk has a through hole.

16. The surgical plate as set forth in claim 15, wherein the trunk has at least two through holes and a trunk waist area between the through holes which encourages bending of the trunk waist area in response to a force applied to at least one of before or during surgery.

17. The surgical plate as set forth in claim 1, further including screws having a threaded shafts and a head wherein the screw holes and the screw heads have a mating interface such that the screw can engage the screw hole so as to allow a plurality of angular orientations of the screw relative to the screw hole.

18. The surgical plate as set forth in claim 1, wherein the trunk has a compression slot.

19. A surgical plate comprising:
   a pre-contoured Y-shaped plate having an inferior surface and a superior surface, the plate consisting of a trunk and pair of a first arm and a second arm,
   the trunk having a linear medial longitudinal axis along the superior surface extending between a first and a second end and wherein the trunk has a compression slot;
   the first arm having a first arm linear medial axis and an ear with at least one screw hole defining a first screw axis, the first ear being attached directly to the trunk by a linking section having a waist, a first angle being defined by an intersection of the medial longitudinal axis of the trunk with the first arm linear medial axis, and a first length being defined by a line from a center of the first arm screw hole along the first arm linear medial axis to the medial longitudinal axis of the trunk,
   the second arm having a second arm linear medial axis and a second ear with at least one second screw hole defining a second screw axis, the second ear being directly attached to the trunk by a linking section having a waist, a second angle being defined by an intersection of the medial longitudinal axis of the trunk with the second arm linear medial axis, and a second length being defined by a line from a center of the second arm screw hole along the second arm linear medial axis to the medial longitudinal axis of the trunk, and the first angle and the first length being different from the second angle and the second length whereby the first screw axis and the second screw axis converge toward the inferior side of the plate but do not intersect.

20. The surgical plate as set forth in claim 19, wherein the compression slot comprises a slot having an internal edge which includes a shoulder that slopes toward the inferior side of the plate as it extends away from the first end of the trunk.

21. The surgical plate as set forth in claim 20, wherein the plate has a superior surface of the trunk which opposes the inferior side of the plate in cross section and the superior surface of the trunk includes a visual indication of the direction in which the compression slot can be used to apply compression.

22. The pre-contoured plate as set forth in claim 19, wherein the through hole does not deform in response to a force applied to at least one of before or during surgery.

23. The pre-contoured plate as set forth in claim 19, wherein the continuous radial curve in the z direction about the longitudinal axis is constant.

24. The pre-contoured plate as set forth in claim 19, wherein the curve forms a portion of a circle.

* * * * *